United States Patent
Senaldi et al.

(10) Patent No.: US 11,214,543 B2
(45) Date of Patent: Jan. 4, 2022

(54) PROCESS FOR THE PREPARATION OF LENVATINIB

(71) Applicant: Indena S.P.A., Milan (IT)

(72) Inventors: Luca Senaldi, Milan (IT); Pietro Allegrini, Milan (IT); Daniele Ciceri, Milan (IT); Anna Bernardi, Milan (IT)

(73) Assignee: Indena S.P.A., Milan (IT)

( * ) Notice: Subject to any disclaimer, the term of this patent is extended or adjusted under 35 U.S.C. 154(b) by 0 days.

(21) Appl. No.: 17/273,740

(22) PCT Filed: Sep. 3, 2019

(86) PCT No.: PCT/EP2019/073442
§ 371 (c)(1),
(2) Date: Mar. 5, 2021

(87) PCT Pub. No.: WO2020/048963
PCT Pub. Date: Mar. 12, 2020

(65) Prior Publication Data
US 2021/0246107 A1  Aug. 12, 2021

(30) Foreign Application Priority Data

Sep. 7, 2018 (EP) ..................................... 18193196

(51) Int. Cl.
*C07D 215/233* (2006.01)

(52) U.S. Cl.
CPC ...... *C07D 215/233* (2013.01); *C07B 2200/13* (2013.01)

(58) Field of Classification Search
CPC ..................... C07D 215/233; C07B 2200/13
See application file for complete search history.

(56) References Cited

U.S. PATENT DOCUMENTS 7,683,172 B2 * 3/2010 Naito ................ C07C 275/34
546/153

FOREIGN PATENT DOCUMENTS

| CN | 104876864 B | 3/2017 |
|---|---|---|
| CN | 106632033 A | 5/2017 |
| EP | 1683785 A1 | 7/2006 |

OTHER PUBLICATIONS

Search Report and Written Opinion of PCT/EP2019/073442 dated Nov. 14, 2019.

* cited by examiner

*Primary Examiner* — John M Mauro
(74) *Attorney, Agent, or Firm* — Silvia Salvadori, P.C.; Silvia Salvadori

(57) ABSTRACT

The present invention relates to a process for the preparation of Lenvatinib of formula (I) from 4-amino-3-chloro-phenol and 4-chloro-7-methoxyquinoline-6-carboxamide.

4 Claims, No Drawings

PROCESS FOR THE PREPARATION OF LENVATINIB

This application is a U.S. national stage of PCT/EP2019/073442 filed on 3 Sep. 2019, which claims priority to and the benefit of European Application No. 18193196.5 filed on 7 Sep. 2018, the contents of which are incorporated herein by reference in their entireties.

The present invention relates to a process for the preparation of Lenvatinib of formula (I) from 4-amino-3-chloro-phenol and 4-chloro-7-methoxyquinoline-6-carboxamide.

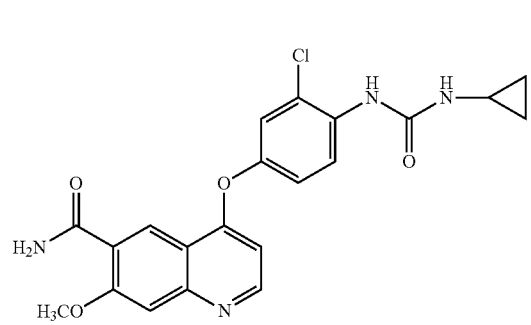

BACKGROUND OF THE INVENTION

Lenvatinib of formula (I), disclosed for the first time in WO0232872, is used as mesylate salt to treat differentiated thyroid carcinoma not responding to treatment with radioactive iodine. Lenvatinib (I) is also active against advanced renal cell carcinoma.

U.S. Pat. No. 7,683,172 discloses a process for the preparation of Lenvatinib (I) from 4-amino-3-chloro-phenol and 4-chloro-7-methoxyquinoline-6-carboxamide which comprises:

1) conversion of 4-amino-3-chloro-phenol (II) into the corresponding phenyl carbamate derivative (III);

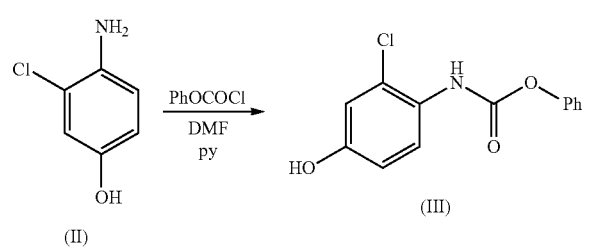

2) reaction of derivative (III) obtained in step (1) with cyclopropylamine to provide a compound of formula (V);

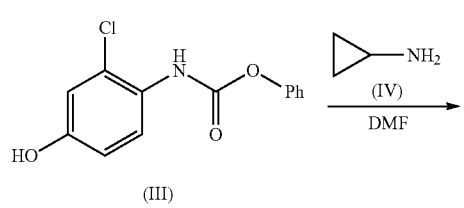

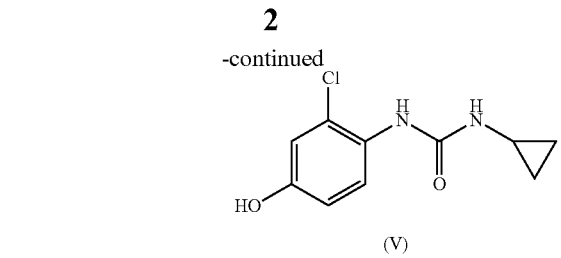

3) coupling reaction between compound (V) obtained in step (2) with 4-chloro-7-methoxyquinoline-6-carboxamide of formula (VI) to provide Lenvatinib (I);

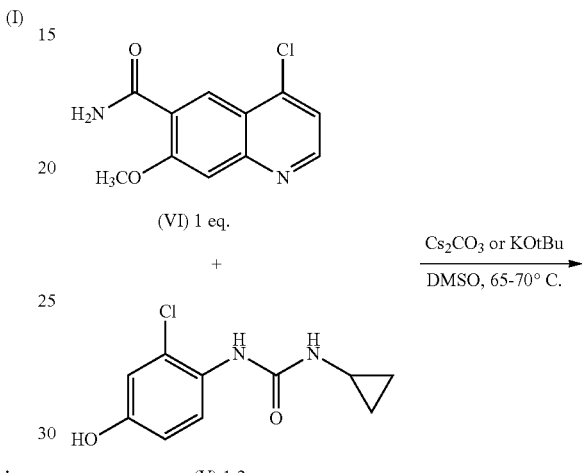

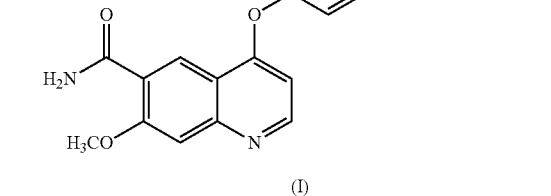

4) crystallization of Lenvatinib (I).

The main drawback of this process lies in step (3) that is performed by mixing 1 eq. of 4-chloro-7-methoxyquinoline-6-carboxamide (VI), 1.2 eq. of the urea derivative (V) obtained in step 2), 2 eq. of cesium carbonate or in alternative 1.2 eq. of sodium tert-butoxide in dimethylsulfoxide at 65-70° C. for 23 h. At the end of the reaction, the product is isolated by crystallization. In these conditions, the precipitate turned out to be contaminated by 1.8% of impurity (VII), 0.5% of impurity (VIII) and 1.7% of impurity (IX). Impurities (VIII) and (IX) are described in CN 107266363. The high amounts of said impurities require an impracticable number of crystallizations with a detrimental effect to the process yield. Therefore, there is still the need for an improved process for the preparation of Lenvatinib (I) which overcomes the above mentioned drawbacks.

(VII)

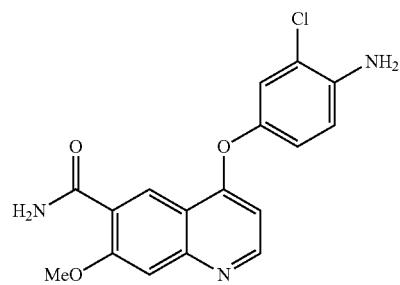

(VIII)

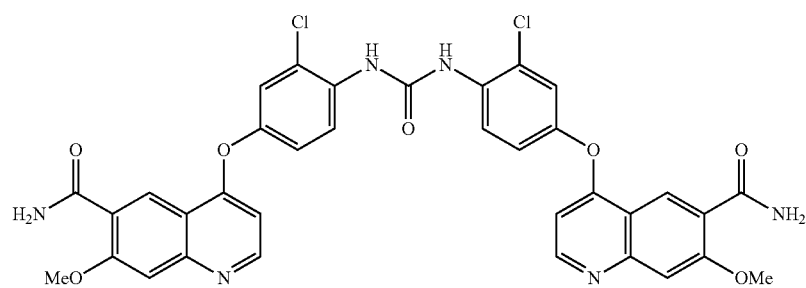

(IX)

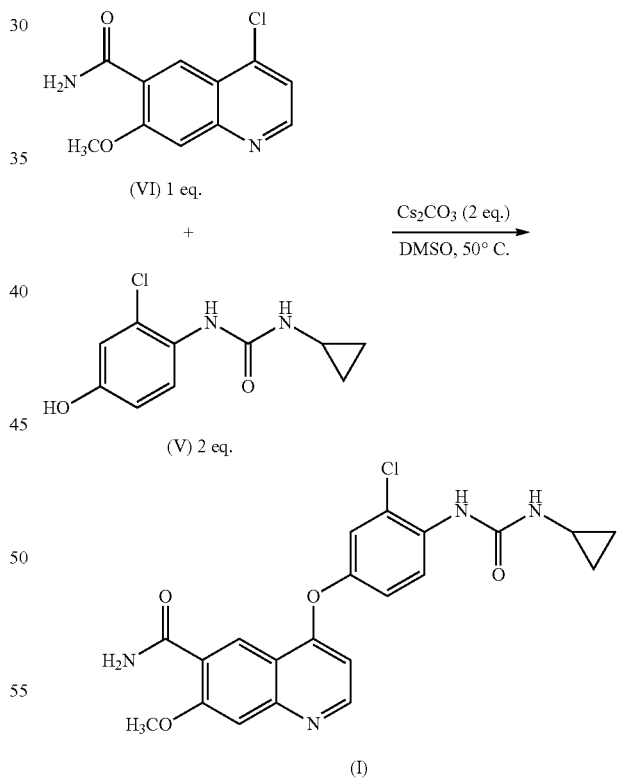

DESCRIPTION OF THE INVENTION

It has now been found that the above-mentioned drawbacks can be overcome by selecting a narrow range of equivalents of reactants and temperatures in the coupling step between 4-chloro-7-methoxyquinoline-6-carboxamide (VI) and the intermediate of formula (V).

Accordingly, the invention relates to a process for the preparation of Lenvatinib of formula (I)

which comprises:

a) reaction of 1 equivalent of 4-chloro-7-methoxyquinoline-6-carboxamide (VI) with 2 equivalents of a compound of formula (V) at a temperature ranging from 45° C. to 55° C., preferably at 50° C., in dimethylsulfoxide (DMSO) and in the presence of cesium carbonate to provide Lenvatinib (I);

b) crystallization of compound (I) in 1:3 DMSO:dichloromethane (DCM).

Step (a) is preferably carried out in the presence of 2 equivalents of cesium carbonate as a base in dimethylsulfoxide at 50° C., preferably for 24 h. The lower reaction temperature and the increased amount of the urea derivative (V) allow to reduce the formation of impurities during the reaction and hence the content of impurities in the final precipitate. Indeed, compound (VII) was reduced from 1.8% to 0.08%, compound (VIII) from 0.5% to 0.15% and compound (IX) from 1.7% to 0.11%. The low levels of impurities at this stage allow to obtain Lenvatinib (I) with HPLC purity=99.6% after recrystallization in 1:3 DMSO:DCM and the corresponding mesylate salt with all the impurities below 0.10%.

Compound (V) is obtained by reaction of 4-amino-3-chloro-phenol (II) with phenyl chloroformate to give phenyl carbamate (III), which is then reacted with cyclopropylamine (IV), according to the following scheme, as disclosed in U.S. Pat. No. 7,683,172:

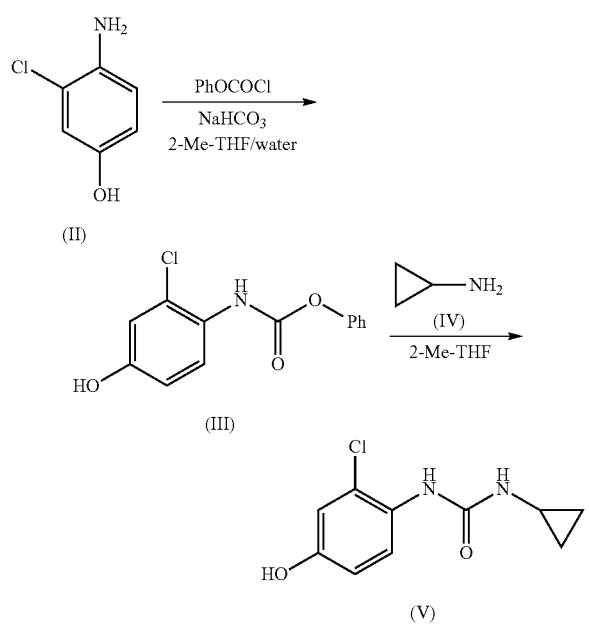

According to a preferred embodiment, the first two steps of the process described in U.S. Pat. No. 7,683,172 are combined in a single step. Specifically, 4-amino-3-chlorophenol is initially converted into phenyl carbamate (III) by reaction with phenyl chloroformate in 2-methyltetrahydrofuran and a saturated sodium bicarbonate solution. When the starting material is consumed, the aqueous phase is separated from the organic phase, which contains compound (III). Cyclopropylamine (IV) is added directly to the organic phase and the mixture is stirred at 50° C. for 3 h. At the end of the reaction, an acidic washing removes the excess of cyclopropylamine (IV). A final crystallization in 4:1 ethyl acetate:heptane allows the removal of phenol and yields the product (V) as white crystals with HPLC purity ≥99.7% and 90% yield.

The following examples illustrate the invention in greater detail.

Example 1-1-(2-Chloro-4-hydroxyphenyl)-3-cyclopropylurea (V)

4-Amino-3-chloro-phenol hydrochloride salt (II) (60.0 g, 333.3 mmol, 1 eq.) was suspended in 2-methyltetrahydrofuran (180 mL, 3V) and the suspension cooled at 0÷5° C. A solution of NaHCO$_3$ (58.8 g, 699.9 mmol, 2.1 eq.) in water (650 mL) was added drop-wise in 25 min. and the temperature maintained below 10° C. A solution of phenyl chloro formate (57.4 g, 46.0 mL, 366.7 mmol, 1.1 eq.) in 2-meth-yltetrahydrofuran (96 mL) was added dropwise in 25 min. keeping the temperature below 10° C. The mixture was stirred at 0÷5° C. for 10 min. The reaction was monitored by quantitative TLC (95:5 DCM: MeOH; UV 254 nm) until 4-amino-3-chloro-phenol was less than 1%.

The phases were separated and removed and cyclopropylamine (IV) (37.9 g, 46.0 mL, 666.6 mmol, 2 eq.) was added drop-wise in 30 min to the organic phase maintaining the temperature below 10° C. The mixture was stirred at 50° C. for 3 h. The reaction course was monitored by quantitative TLC (7:3 hexane:EtOAc, UV 254 nm) until phenyl carbamate intermediate (III) was less than 0.5%.

The reaction mixture was cooled to r.t. and 1M H$_2$SO$_4$ (200 mL) was added in 15 min. The aqueous phase was removed and the organic phase was diluted with 2-methyltetrahydrofuran (60 mL, 1V), washed with 10% NaCl (200 mL) and with H$_2$O (50 mL). The organic phase was concentrated to 120 mL (2V) at T$_{ext}$=50° C. and P=150 mbar. Ethyl acetate (240 mL, 4V) was added and the resulting mixture concentrated to 240 mL (4V). Ethyl acetate (120 mL, 2V) was added and the mixture concentrated to 240 mL (4V). The latter operation was repeated twice. The obtained slurry was stirred at r.t. for 1 h and n-heptane (60 mL, 1V) was added. After 30 min., the precipitate was filtered, washed with 4:1 EtOAc:n-heptane (60 mL, 1V) and with n-heptane (60 mL, 1V). The white solid was dried at 55° C. under vacuum for 16 h to yield 1-(2-chloro-4-hydroxyphenyl)-3-cyclopropylurea (V) (68.5 g, y=91%). Typical HPLC purity is 99.74-99.93%.

$^1$H-NMR (400 MHz, DMSO-d$_6$) δ (ppm):0.38 (2H, m), 0.61 (2H, m), 2.50 (1H, m,), 6.65 (1H, dd, J=8.9 Hz, J=2.8 Hz,), 6.77 (1H, d, J=2.8 Hz), 6.79 (1H, d, J=2.6 Hz), 7.53 (1H, s), 7.68 (1H, d, J=8.9 Hz), 9.44 (1H, s).

Comparative Example 2-4-(3-Chloro-4-(cyclopropylaminocarbonyl)-aminophenoxy)-7-methoxy-6-quinolinecarboxamide (I) (Coupling Conditions According to Example 3 of U.S. Pat. No. 7,683,172)

4-chloro-7-methoxyquinoline-6-carboxamide (VI) (0.983 g, 4.15 mmol, 1 eq.) and 1-(2-chloro-4-hydroxyphenyl)-3-cyclopropylurea (V) (1.13 g, 4.99 mmol, 1.2 eq.) were suspended in 20 mL of DMSO. Cesium carbonate (2.71 g, 8.32 mmol, 2 eq) was added and the mixture was stirred at 70° C. for 23 h. The reaction mixture was cooled to r.t. and water (50 mL) added to precipitate the product. The precipitated crystals were filtered off and dried to afford a dark blue solid (1.58 g, 3.70 mmol, y=89%, impurities content reported in Table 1). Crude Lenvatinib (1.58 g, 3.70 mmol) was dissolved in DMSO (7.8 mL, 5V) at 70° C. The solution was cooled to r.t. and dichloromethane (23.7 mL, 15V) was added in 15 min. The mixture was stirred at r.t. for 16 h and at 0÷5° C. for 1 h. The suspension was filtered, the solid washed with 1:3 DMSO:DCM (3.1 mL, 2V) and triturated with pure DCM (6.2 mL, 4 V) three times. The solid was dried at 60° C. under vacuum for 24 h to yield Lenvatinib (I) (34.07 g, 79.81 mmol, crystallization yield=79%, total yield=67%). Typical A% HPLC purity is 99.6%.

(1.09 g, 2.55 mmol, crystallization yield=69%, total yield=62%). Typical A% HPLC purity is 95.0% Impurities content is reported in Table 1.

$^1$H-NMR (400 MHz, DMSO-d$_6$) δ (ppm):0.43 (2H, m), 0.65 (2H, m), 2.57 (1H, m), 4.08 (3H, s), 6.46 (1H, d, J=6.6 Hz), 7.18 (1H, brs), 7.25(1H, dd, J=2.8 Hz, J=9.1 Hz), 7.48

(1H,d, J=2.8 Hz), 7.52 (1H, s), 7.70 (1H, s), 7.83 (1H, s), 7.96 (1H, s), 8.25 (1H, d, J=9.1 Hz), 8.63 (2H, m).

Example 3-4-(3-Chloro-4-(cyclopropylaminocarbonyl)aminophenoxy)-7-methoxy-6-quinolinecarboxamide (I)

4-chloro-7-methoxyquinoline-6-carboxamide (VI) (32.0 g, 135.2 mmol, 1 eq.) and 1-(2-chloro-4-hydroxyphenyl)-3-cyclopropylurea (V) (61.30 g, 270.4 mmol, 2 eq.) were suspended under nitrogen in DMSO (192 mL, 6V). Cesium carbonate (88.11 g, 270.4 mmol, 2 eq) was added and the mixture was stirred at 50° C. under a nitrogen atmosphere for 24 h. The reaction mixture was cooled to r.t. and water (192 mL, 6V) added drop-wise in 40 min. to precipitate the product. The obtained suspension was stirred at r.t for 1 h. The precipitated crystals were filtered off, washed with 1:1 DMSO:$H_2O$ (64 mL, 2V) and triturated three times with water (130 mL, 4V). The solid was dried at 60° C. under vacuum for 18 h to afford a light brown/grey solid (53.25 g, 124.7 mmol, y=85%, impurities content reported in Table 1). Crude Lenvatinib (53.25 g, 124.7 mmol) was dissolved in DMSO (450 mL, 5V) at 70° C. The solution was cooled to r.t. and dichloromethane (1350 mL, 15V) was added in 15 min. The mixture was stirred at r.t. for 16 h and at 0±5° C. for 1 h. The suspension was filtered, the solid washed with 1:3 DMSO: DCM (106 mL, 2V) and triturated with pure DCM (210 mL, 4 V) three times. The solid was dried at 60° C. under vacuum for 24 h to yield Lenvatinib (I) (34.07 g, 79.81 mmol, crystallization yield=79%, total yield=67%). Typical A% HPLC purity is 99.5% and impurities content is reported in Table 1.

$^1$H-NMR (400 MHz, DMSO-$d_6$) δ (ppm):0.43 (2H, m), 0.65 (2H, m), 2.57 (1H, m), 4.08 (3H, s), 6.46 (1H, d, J=6.6 Hz), 7.18 (1H, brs), 7.25(1H, dd, J=2.8 Hz, J=9.1 Hz), 7.48 (1H,d, J=2.8 Hz), 7.52 (1H, s), 7.70 (1H, s), 7.83 (1H, s), 7.96 (1H, s), 8.25 (1H, d, J=9.1 Hz), 8.63 (2H, m).

TABLE 1

HPLC content of impurities with selected coupling conditions

| Impurities | First precipitate (1:1 DMSO:$H_2O$) | | Lenvatinib recrystallized in 1:3 DMSO:DCM | |
|---|---|---|---|---|
| | Example 2 | Example 3 | Example 2 | Example 3 |
| VII | 1.81% | 0.08% | 1.02% | 0.04% |
| VIII | 0.46% | 0.15% | 0.22% | 0.05% |
| IX | 1.74% | 0.11% | 1.61% | 0.05% |

Example 4-Crystalline Form of the mesylate salt of 4-(3-chloro-4-(cyclopropylaminocarbonyl)aminophenoxy)-7-methoxy-6-quinolinecarboxamide Lenvatinib free base (6.81 g, 15.9 mmol, 1 eq.) obtained according to Example 3 was suspended in acetic acid (18.4 mL, 2.7 V) and methanesulfonic acid (1.0 mL, 15.9 mmol, 1 eq.) diluted in acetic acid (2 mL, 0.3V) was added. The mixture was stirred at 60° C. for 30' to reach complete dissolution. The solution was passed through Whatman 0.2 μm filter and heated again at 60° C. Ethyl acetate (6.8 mL, 1 V) was added drop-wise and the mixture cooled to 40° C. The mixture was stirred at 40° C. for 16 h and at r.t. for 1 h. The suspension was filtered and the solid washed with 3:1 acetic acid:EtOAc (6.8 mL, 1V). The wet solid (ACA-1 form, 18.25 g) was dried at 60° C. in vacuum for 72 h and at 70° C. for additional 24 h to afford the title compound as ACA-1-HT dry solid form (6.22 g, 11.9 mmol, y=75%). Typical A% HPLC purity is 99.8%.

$^1$H-NMR (DMSO-$d_6$) δ (ppm): 0.43 (2H, m, $H_{9'A}$,$H_{10'A}$), 0.65 (2H, m, $H_{9'B}$, $H_{10'B}$), 2.40 (3H, s, $CH_3SO_3H$), 2.57 (1H, m, $H_{8'}$), 4.08 (3H, s, OMe), 6.96 (1H, d, J=6.6 Hz, $H_3$), 7.25 (1H, brs, $NH_{8'}$), 7.35 (1H, dd, J=2.8 Hz, J=9.1 Hz, $H_{6'}$), 7.62 (1H,d, J=2.8 Hz, $H_{2'}$), 7.70(1H, s, $H_8$), 7.87 (1H, s, $NH_{10}$), 7.94 (1H, s, $NH_{10}$), 8.06 (1h, s, $NH_{4'}$), 8.34 (1H, d, J=9.1 Hz, $H_{5'}$), 8.71 (1H, s, $H_5$), 8.97 (1H, d, J=6.6 Hz, $H_2$).

The invention claimed is:
1. A process for the preparation of Lenvatinib of formula (I)

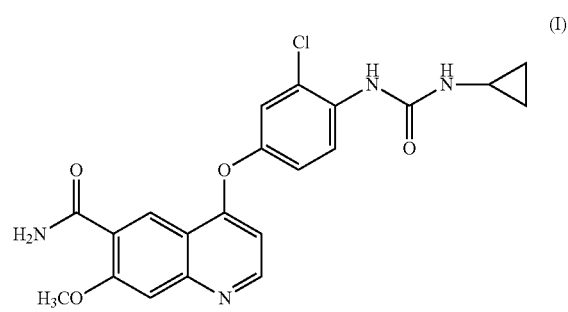 [SMILES: COc1cc2nccc(Oc3ccc(NC(=O)NC4CC4)c(Cl)c3)c2cc1C(N)=O]

which comprises:
a) reacting 1 equivalent of 4-chloro-7-methoxyquinoline-6-carboxamide (VI) with 2 equivalents of the compound of formula (V) at a temperature ranging from 45° C. to 55° C., in dimethylsulfoxide and in the presence of cesium carbonate to provide Lenvatinib (I);

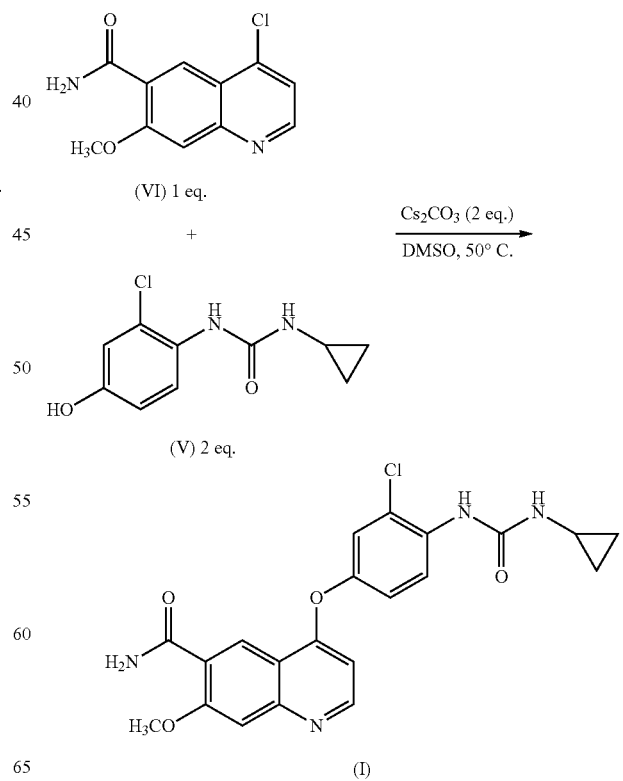

b) crystallizing Lenvatinib (I) in 1:3 dimethylsulfoxide: dichloromethane.

2. The process according to claim 1 wherein step a) is carried out at 50° C.

3. The process according to claim 1 wherein step a) is carried out in the presence of 2 equivalents of cesium carbonate.

4. The process according to claim 1 wherein compound (V) is obtained by:

reacting 4-amino-3-chloro-phenol (II) with phenyl chloroformate in 2-methyltetrahydrofuran in the presence of a saturated sodium bicarbonate solution to provide an aqueous phase and an organic phase which contains the compound of formula (III), separating the aqueous phase and adding cyclopropylamine (IV) to the organic phase

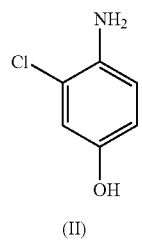

(II)

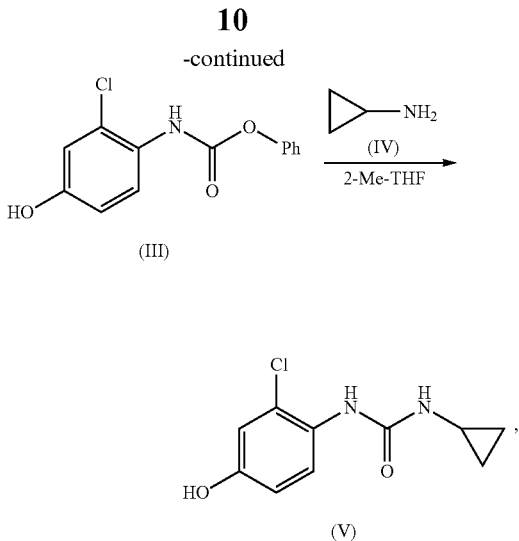

acidic washing and crystallizing in 4:1 ethyl acetate: heptane.

* * * * *